United States Patent [19]

Androphy

[11] Patent Number: 4,487,203

[45] Date of Patent: Dec. 11, 1984

[54] TRIPLANAR KNEE RESECTION METHOD

[76] Inventor: Gary W. Androphy, P.O. Box 533, Gurnee, Ill. 60031

[21] Appl. No.: 317,875

[22] Filed: Nov. 3, 1981

[51] Int. Cl.$^3$ .............................................. A61B 17/00
[52] U.S. Cl. .............................. 128/303 R; 128/92 R; 33/174 D
[58] Field of Search ................... 128/305, 303 R, 317, 128/92 E, 92 H; 33/174 D

[56] References Cited

U.S. PATENT DOCUMENTS 4,211,228  7/1980  Cloutier ........................... 128/303 R

OTHER PUBLICATIONS

"Knee Replacement Using the Insall/Burstein Total Condylar Knee System" 1980.
"R.M.C. Total Knee System" 1978 Richards Manufac. Co.
Insall et al., "Total Condylar Prosthesis Surgical Technique" 1976.
Insall, "Total Condylar Knee Prosthesis Surgical Technique" 1978.
Ranawat, "Total Condylar Knee Prosthesis Surgical Technique" 1978.
Murray, "Variable Axis Total Knee Surgical Technique" 1977 & 1980.
"The Howmedica Universal Total Knee Instrument System" 1980.
"The Howmedica Kinematic Knee System", Ewald et al., 1981.
"The Howmedica Kinematic Knee System", Brochure 1981.
"Geo-Patella/Geo-Tibial Total Knee" 1977.
"Multi-Radius Total Knee" 1978.
"The Multi-Radius Total Knee with Surgeon-Guided Instrumentation" 1978.
"Cloutier (Non-Constrained) Total Knee" 1979.

Primary Examiner—Michael H. Thaler
Attorney, Agent, or Firm—Arnold, White & Durkee

[57] ABSTRACT

An improved triplanar knee resection system is provided for preparing a knee joint for a prosthesis. The apparatus of the triplanar knee system includes a single guide member for use in resecting the distal femoral condyles, the proximal tibia, and the distal femur. The guide member cooperates with a simplified set of instruments, including femur and tibia guide rods, a tibia adaptor, a tibia bar, and a femur bar, for establishing equal flexion and extension gaps and triplanar resections. The method of the triplanar knee system provides a simplified procedure for use by an orthopedic surgeon in properly preparing a knee joint for implantation of a prosthesis.

8 Claims, 16 Drawing Figures

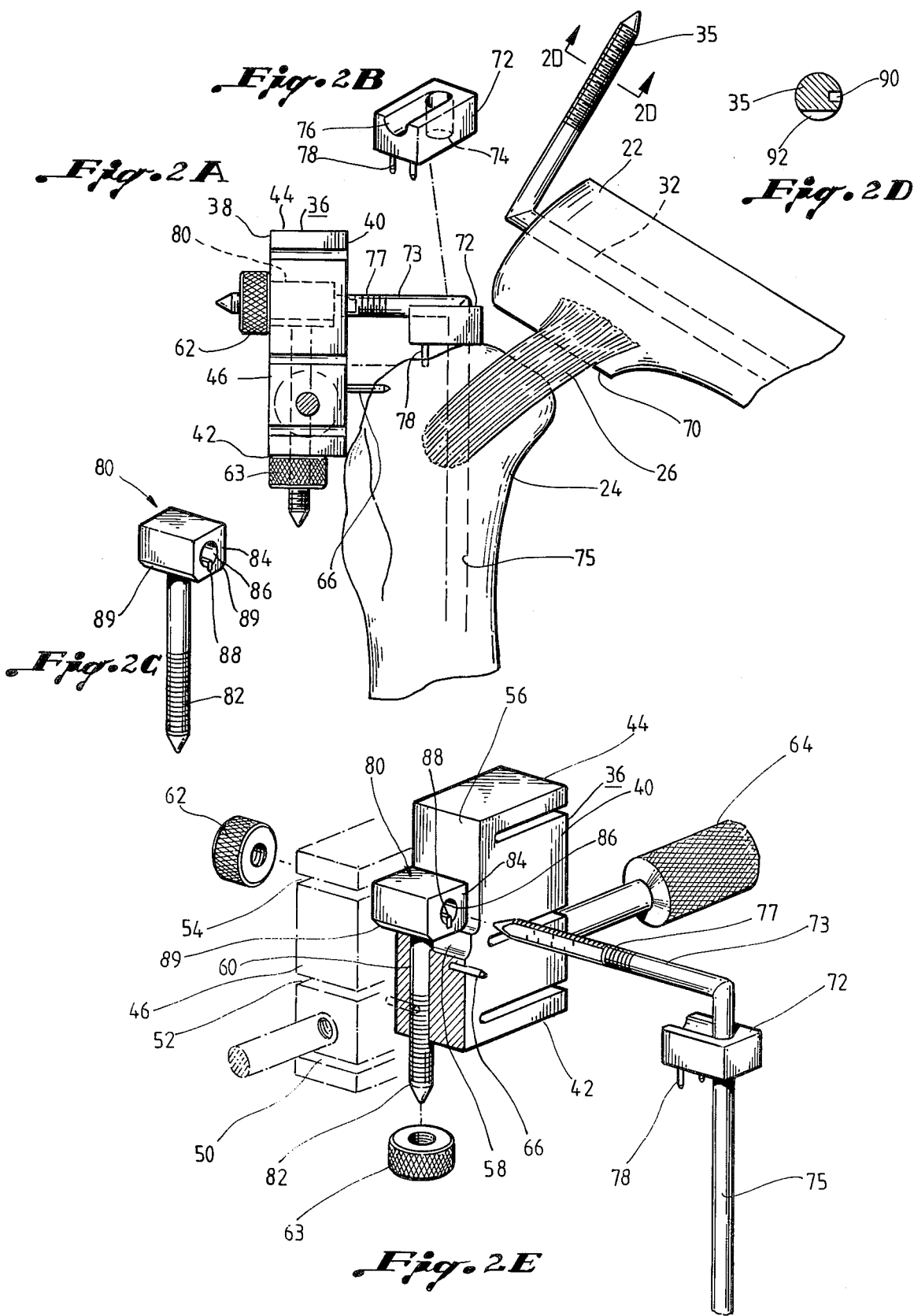

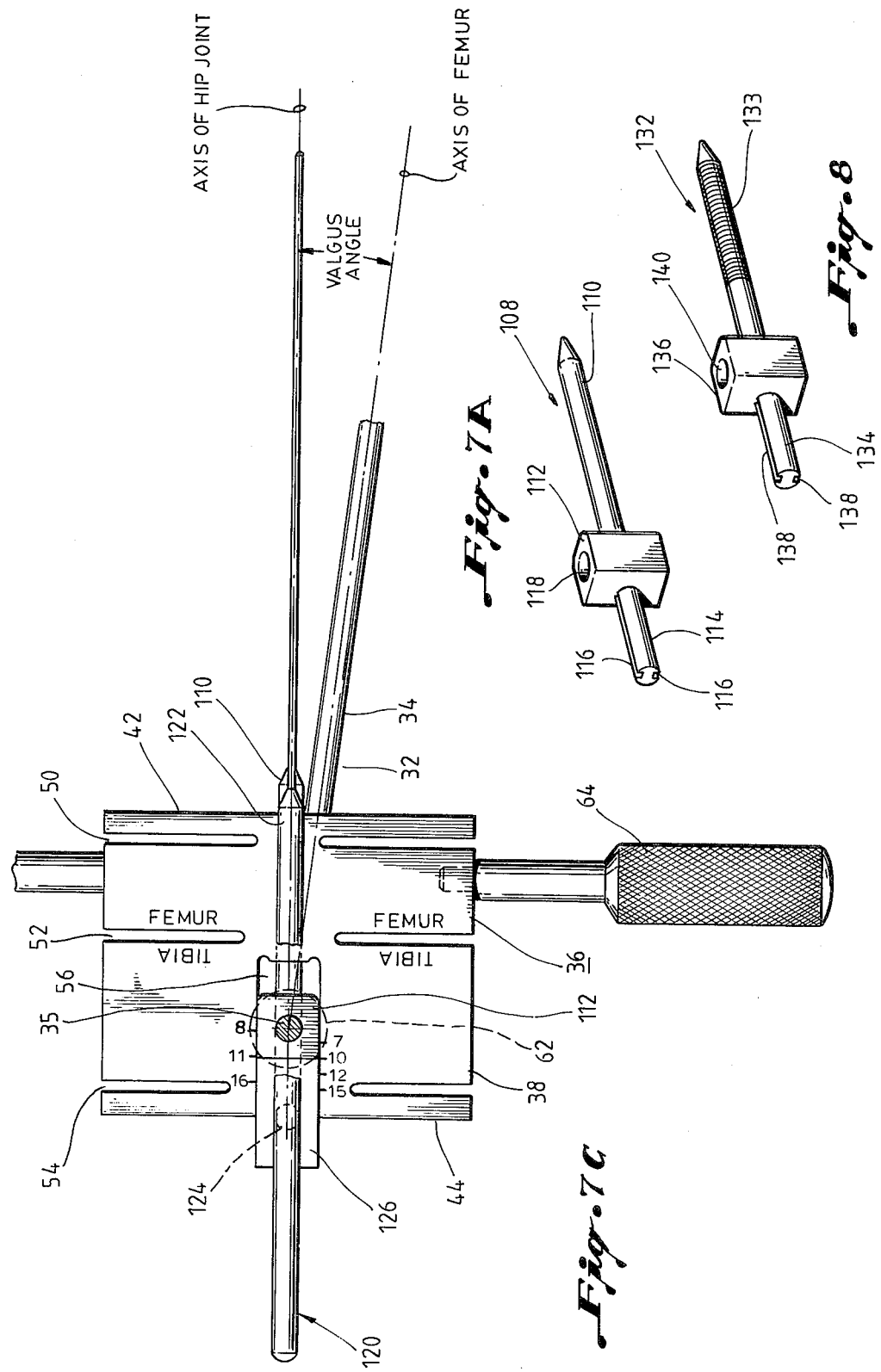

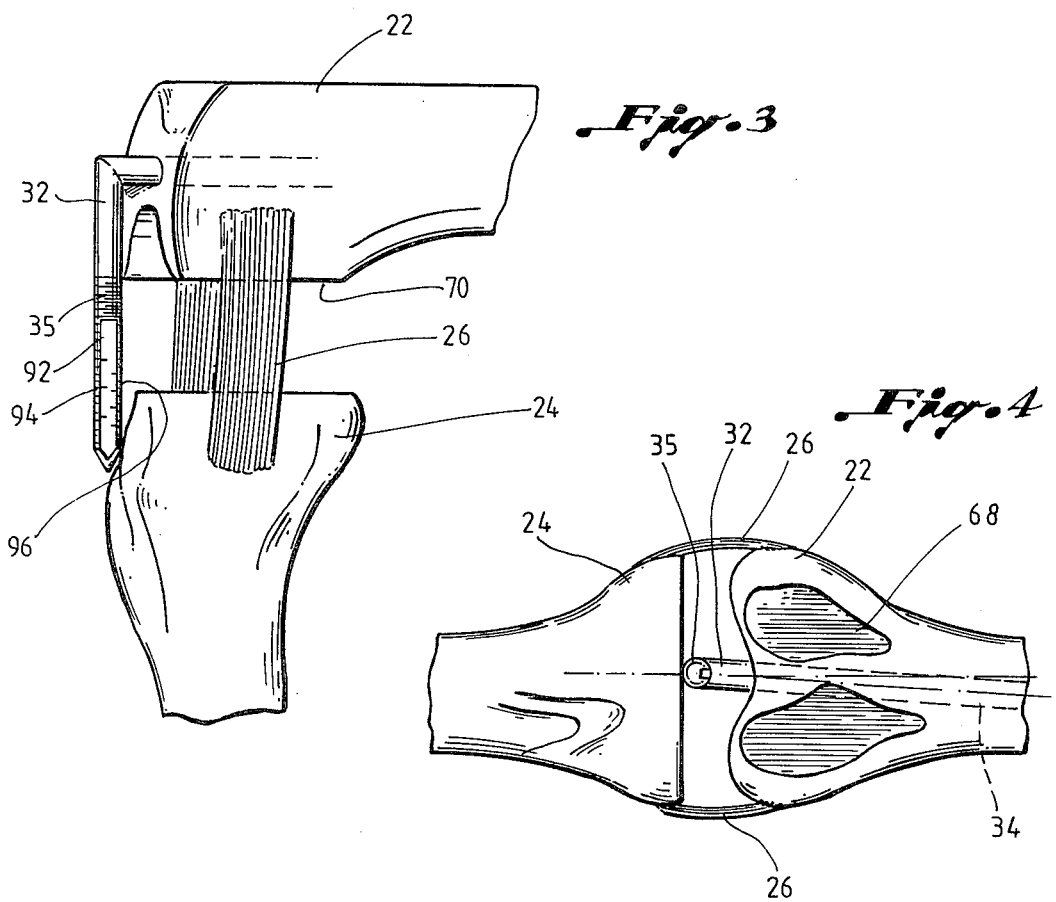
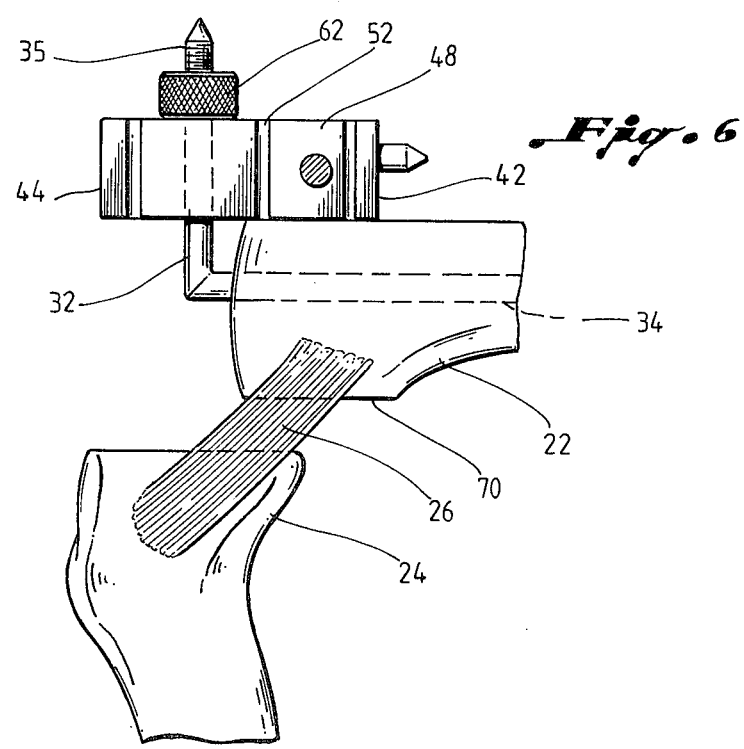

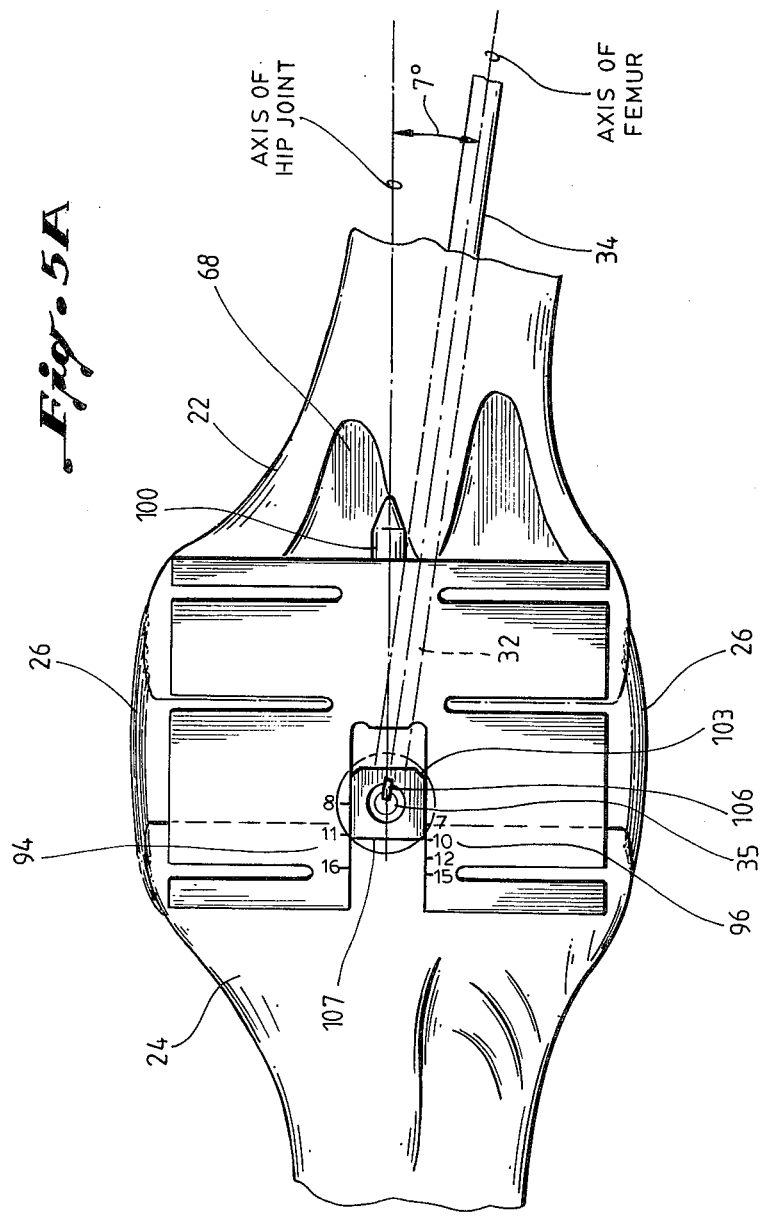

TRIPLANAR KNEE RESECTION METHOD

BACKGROUND

The invention relates generally to knee surgical techniques and, more particularly, to apparatus and method for resection of the knee joint for a knee prosthesis.

Replacement of a knee joint with a prosthesis involves a comprehensive surgical procedure, as is known to those skilled in the art. The surgical procedure is complicated by the fact that only a relatively small area of the patient's leg, namely the knee, is exposed during the operation. The remainder of the patient's leg, as well as most of his body, is covered with sterile drapes. The R.M.C. TM Total Knee System technique manual published by Richards Manufacturing Company, Inc., 1450 Brooks Road, Memphis, Tenn. 38116 illustrates this aspect of the surgical procedure. The surgical procedure is further complicated by the presence of the muscle and skin tissue which surrounds the knee joint.

Once the knee joint is exposed by known techniques, the distal femur and proximal tibia must be prepared to enable implantation of the prosthesis. Such preparation includes resection of the anterior and posterior distal femoral condyles, the proximal tibia, and the distal femur. In order to achieve proper stability of the knee prosthesis when implanted, the aforementioned resections must be accurately aligned relative to an imaginary axis extending through the hip joint, knee joint, and ankle joint.

It is necessary for the distal femoral condylar resections to be parallel to the proximal tibial resection when the knee is in flexion and for the proximal tibial resection when the knee is in extension. These "triplanar" resections should be made to provide equal flexion and extension gaps, i.e., the distance between the posterior femoral condylar resection and the proximal tibial resection with the knee in flexion (the flexion gap) should be equal to the distance between the distal femoral resection and the proximal tibial resection with the knee in extension (the extension gap). Furthermore, the resected proximal tibia and resected distal femur should be perpendicular to the above-referenced imaginary axis when the knee is extended.

The necessity of accurately making the triplanar resections has led to the development of relatively complicated instrumentation to aid the orthopedic surgeon. Illustrative of such instrumentation are the Howmedica® Universal TM Total Knee Instrument System as shown in the catalogue published by Howmedica, Inc., Orthopaedics Division, 359 Veterans Blvd., Rutherford, N.J. 07070 and the Insall/Burstein surgical instrument system as designed by John Insall, M.D. and Albert H. Burstein, Ph.D. and shown in the publication entitled "Knee Replacement Using the Insall/Burstein Total Condylar Knee System."

Although providing some guidance to the orthopedic surgeon, these prior instrument systems utilize long alignment rods which have proved to be less than satisfactory under sterile operating room conditions, as described previously. Furthermore, such instrument systems include numerous components which still require much manual manipulation and which are cumbersome to use.

SUMMARY

In accordance with the present invention, an improved triplanar knee resection system, free of many disadvantages of the prior art, is provided. The triplanar knee system includes a single guide member for use in making the proper bone resections. The guide member includes an alignment opening for cooperating with a guide rod. The guide rod has a 90° angle bend and is adapted to be inserted into the femur for use in aligning the guide member. In one aspect of the present invention, the guide rod is designed such that it remains inserted in the femur during the surgical procedure, thereby establishing a common reference point for the bone resections.

The guide member includes three pairs of parallel guide slots which are utilized in making the triplanar bone resections. The guide member cooperates with the guide rod to enable resection of the knee joint with the knee always in flexion.

A second identical guide rod is provided along with a tibia adapter and a tibia bar for use with the guide member in resecting the proximal tibia. A femur bar is provided for use with the guide member and femur guide rod in making the resection of the distal femur.

In a second aspect of the present invention, the femur guide bar is designed to compensate for the appropriate valgus angle of the femur relative to an imaginary axis extending through the hip joint, knee joint, and ankle joint. In another aspect of the present invention, the triplanar knee system achieves equal flexion and extension gaps of the resected knee joint. In still another aspect, the triplanar knee system ensures proper alignment of the distal femoral resection and the proximal tibial resection although these two resections are independently aligned.

In a method aspect of the invention, a common reference is established for resecting the anterior and posterior distal femoral condyles and the distal femur. This common reference is used to provide equal flexion and extension gaps.

In another aspect of the method, the alignment of the guide member for resecting the distal femur is accomplished without the use of any "eyeball" techniques.

BRIEF DESCRIPTION OF THE DRAWINGS

These and other advantages and features of the present invention will become apparent from the following detailed description considered in connection with the appended drawings in which like parts are given identical reference numerals and in which:

FIG. 2A is a side view of the guide member cooperating with a second guide rod, a tibia adaptor, and a tibia bar for resecting the proximal tibia in accordance with the present invention;

FIG. 2B is an illustrative view of the tibia adaptor of FIG. 2A;

FIG. 2C is an illustrative view of the tibia bar of FIG. 2A;

FIG. 2D is a cross section of the tibia guide rod taken along section line 2D—2D in FIG. 2A;

FIG. 2E is an illustrative view of the rear side of the triplanar guide member of FIG. 2A, partially cut away for detail;

FIG. 3 is an illustrative view of the femoral guide rod being used to determine the flexion gap in accordance with the present invention;

FIG. 4 is a top view of the femoral guide member being used to establish an extension gap equal to the flexion gap in accordance with the present invention;

FIG. 5A is a top view of the guide member cooperating with the femoral guide rod and a femur bar for proper positioning of the guide member with the knee extended in accordance with the present invention;

FIG. 5B is an illustrative view of the femur bar of FIG. 5A;

FIG. 6 is a side view of the guide member cooperating with the femoral guide rod and femur bar with the knee in flexion in accordance with the present invention;

FIG. 7A is an illustrative view of a modified femur bar;

FIG. 7C is a schematic diagram of the modified femur bar cooperating with the pointer and the guide member to establish the proper valgus angle in accordance with the present invention; and FIG. 8 is an illustrative view of a modified tibia bar for use with the pointer of FIG. 7B.

DETAILED DESCRIPTION

Figure 1A:
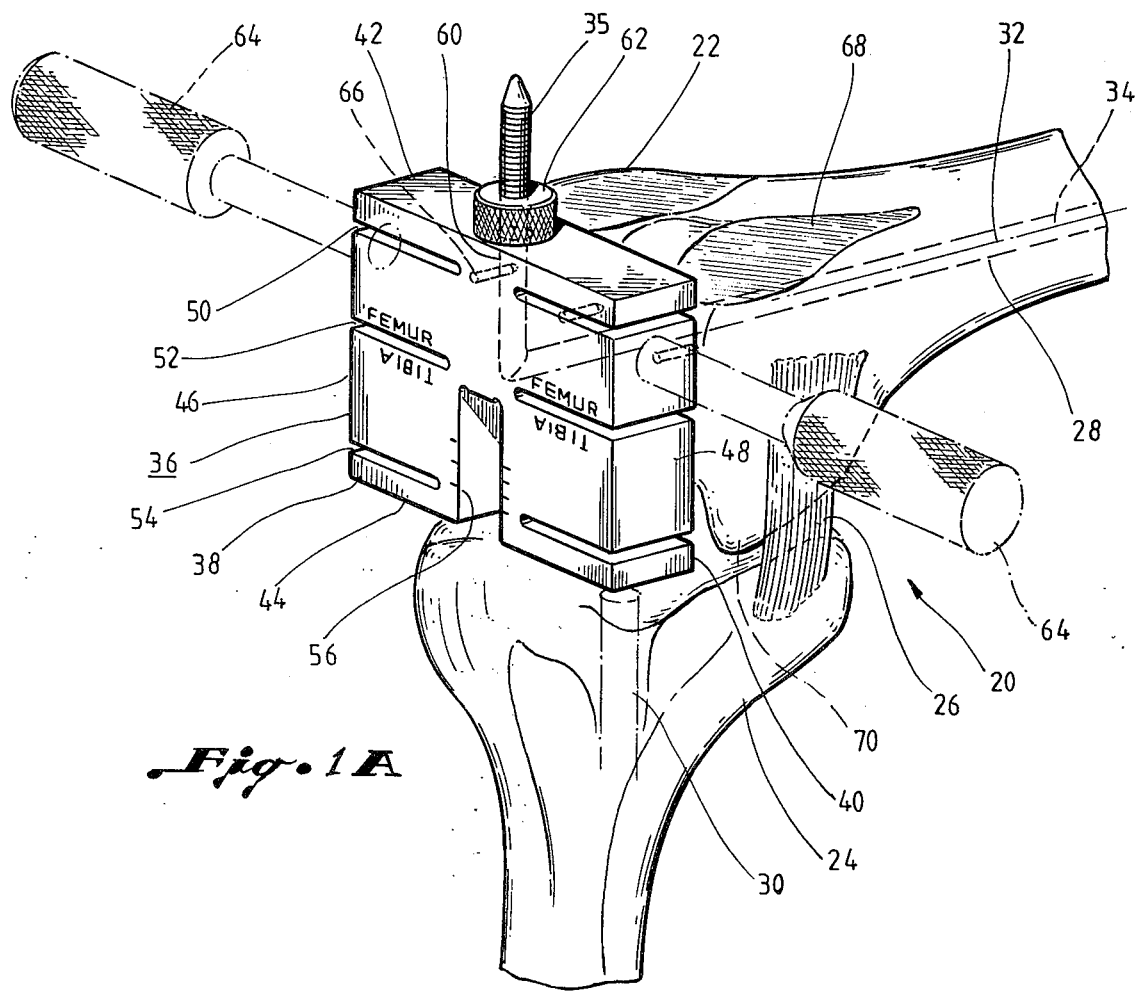
FIG. 1A is an illustrative view of a triplanar guide member cooperating with a guide rod for making the distal femoral condylar resections in accordance with the present invention.
Figure 1B:
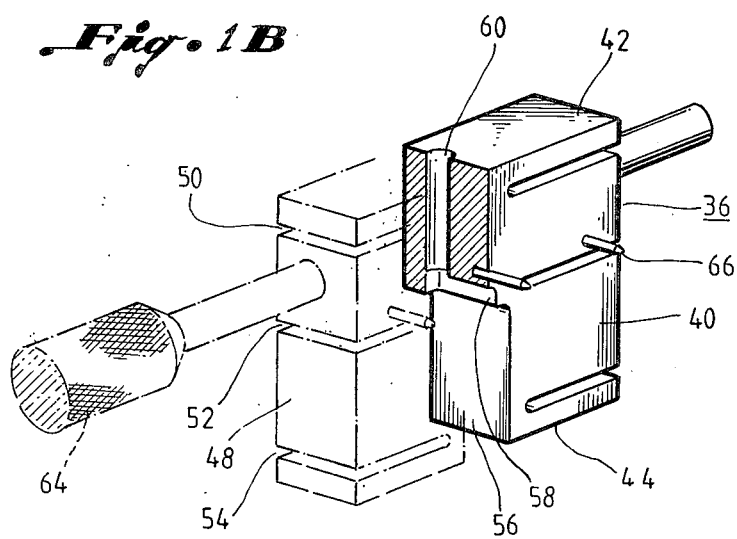
FIG. 1B is an illustrative view, partially cut away for detail, of the rear side of the triplanar guide member of FIG. 1A.

Referring now to FIGS. 1A and 1B, shown is a knee joint 20 including a distal femur 22 and proximal tibia 24 in flexion. It is to be understood that the exposure of the distal femur and proximal tibia is achieved by known surgical techniques. Such known techniques may include removal of the anterior and posterior cruciate ligaments (not shown). However, the present invention is applicable in making bone resections for a cruciate sparing prosthesis as well.

A pair of collateral ligaments 26, which connect the distal femur 22 and proximal tibia 24, are left in place. It is to be understood that any necessary ligamentous release may be preformed by known surgical techniques before making the appropriate bone resections for replacement of the knee.

In accordance with the present invention, with the knee in flexion, a first hole 28 is drilled into the end of distal femur 22, approximately centered in the medullary canal by known techniques. Likewise, a second hole 30 is drilled into the end of proximal tibia 24, slightly anterior relative to the centerline extending into the medullary canal of the tibia.

A femur guide rod 32 having a longer portion 34 and a shorter, threaded portion 35 forming an L-shaped is inserted into a triplanar guide member 36. Guide member 36 has a generally rectangular configuration with a front surface 38, a rear surface 40, a top surface 42, a bottom surface 44, a left surface 46, and a right surface 48. Guide member 36 includes three pairs of resection guide slots 50, 52, 54 which are utilized to make the appropriate bone resections. A vertical guide slot 56 is centrally located in the guide member relative to sides 46, 48. Guide slot 56 forms a guide rod recess 58 at its upper end. A vertical bore 60 extends upward from guide rod recess 58 through guide member 36. Guide rod recess 58 and bore 60 are configured to matingly receive threaded portion 35 of guide rod 32 and to stabilize the guide rod with respect to guide member 36. The guide rod is secured in place with a circular nut or cap 62, which is threaded onto threaded portion 35 of the guide rod until the nut or cap abuts top surface 42 of guide member 36.

Guide member 36 may be provided with a pair of handles 64. It is to be understood that handles 64 may be integrally formed with guide member 36 or may be threadably connected to the guide member and still remain within the contemplation of the present invention. Guide member 36 is also provided with a plurality of pins 66 protruding outwardly from rear side 40. Pins 66 are adapted to anchor the guide member into the bone to prevent the guide member from rotating during use.

As shown in FIG. 1A, femur guide rod 32 is inserted into drilled hole 28. Before pressing pins 66 into the end of distal femur 22, guide member 36 is manually oriented to obtain the proper alignment of the guide member relative to the anterior and posterior distal femoral condyles, identified as 68 and 70, respectively, as is known to those skilled in the art. When aligned, guide members pins 66 are pressed into the distal femur. Anterior distal femoral condyles 68 are resected with an oscillating saw (not shown) or the like by using upper guide slots 50. Likewise, posterior distal femoral condyles 70 are resected with an oscillating saw with the aid of bottom guide slots 54. The guide member and guide rod are then pulled partially out to disengage pins 66, and guide member 36 is then removed from guide rod 32 after removing cap 62. Preferably, femur guide rod member 32 is then pushed back into hole 28 and remains there for later resection of the distal femur. It is to be understood, however, that guide rod 32 may be removed from the femur and reinserted later for use in resecting the distal femur. Any remaining portion of the anterior or posterior distal femoral condyles, such as in the center region where the guide slots do not extend, may then be removed by using the previously resected bone portions as a leveling guide.

The proximal tibia is then subluxed to its forward position, as shown in FIG. 2A. A tibia guide rod adapter 72 is slidably disposed onto a longer portion 75 of a second guide rod 73, which is identical to the first guide rod that remains inserted in the femur during this stage of the procedure. As shown in FIG. 2B, adapter 72 has an opening 74 which cooperates with a recess 76 to stabilize guide rod 73 relative to the adapter. Tibia adapter 72 is provided with a pair of pins 78, which are pressed into the end of the proximal tibia to prevent the guide rod from rotating about the longitudinal axis extending through longer portion 75. The guide rod carrying the tibia adapter 72 is inserted into drilled hole 30, and a shorter portion 77 of guide rod 73 is manually oriented such that a plane extending through the L-shaped guide rod is parallel to the sagittal plane extending through the tibia. When properly aligned, the guide rod is pushed further into hole 30, thereby implanting tibia adapter pins 78 and preventing rotation of guide rod 73.

A tibia bar 80 having an extended threaded portion 82 and a generally rectangular base 84, as shown in FIG. 2C, is inserted into vertical guide slot 56 of guide member 36 such that threaded portion 82 extends through vertical bore 60 in the guide member. A second cap 63 is threaded partially onto the threaded portion of tibia bar 80. The rectangular base of the tibia bar has a bore 86 extending lengthwise therethrough, and a key lock 88 protrudes from the bottom center of bore 86. The bottom edges of base 84 are slightly chamfered, as shown at 89. Guide member 36 with the tibia bar inserted therein is inverted, and the guide member and tibia bar are inserted onto threaded portion 77 of guide rod 73. The shorter portion of the guide rod includes a key seat 90 (see FIG. 2D) which cooperates with key lock 88 to properly align the guide member 36 for resecting the proximal tibia. FIG. 2E illustrates the cooperation of guide member 36, tibia bar 80, guide rod 73, and tibia adaptor 72.

In order to properly align the guide member for resection of the proximal tibia, cap 63, threaded onto the threaded portion 82 of tibia bar 80, is either loosened or tightened to lower (by gravity) or raise center guide slots 52 of the guide member relative to the proximal tibia. When properly positioned, the guide member and tibia bar are pushed further onto shorter portion 77 of the guide rod, thereby implanting pins 66 in the anterior side of the proximal tibia. Cap 62, threaded onto shorter portion 77, is then tightened. An oscillating saw is inserted through center slots 52 of the guide member, and the proximal tibia is then resected. Cap 62, threaded onto the guide rod, is then loosened, guide member pins 66 are disengaged, and guide rod 73 supporting the guide member and tibia bar 80 is then removed, along with tibia adapter 72. Any remaining portion of the proximal tibia may then be leveled by using the previously resected portions as a leveling guide.

Having now completed two of the triplanar resections, the flexion gap between the resected proximal tibia and the resected posterior distal femur is determined. As shown in FIG. 3, threaded portion 35 of the guide rod 32, which remained inserted in the femur during resection of the proximal tibia, is oriented in a direction perpendicular to the resected surface of the proximal tibia. Threaded portion 35 has a flat portion 92 along one side thereof. Flat portion 92 has two sets of marks 94, 96 which indicate the relative thicknesses of various tibial components for knee prostheses, such as those manufactured and sold under the names of Howmedica ® Universal ™ Total Knee Instrument System and Insall/Burstein Total Condylar Knee System. The marks are located at predetermined positions along the flat portion 92 of the guide rod to indicate the proper tibial component to be utilized in the knee prosthesis. With collateral ligaments 26 extended taughtly, the flexion gap is determined by verifying which mark is level with the resected surface of the proximal tibia. It is to be understood that any set of marks corresponding to a particular brand of tibial component may be utilized and still remain within the contemplation of the present invention.

Once the flexion gap is determined by selecting the appropriate tibial component mark, the knee is temporarily placed in extension, as shown in FIG. 4. The guide rod is then positioned with shorter portion 35 extending upward and perpendicular to resected anterior distal femur 68 such that the outer edge of the shorter portion rests upon the resected proximal tibia when collateral ligaments 26 are extended taughtly.

Referring now to FIGS. 5A and 5B, with the knee in extension, a femur bar 98 having a smooth extended portion 100 and a generally rectangular base 102 is inserted into guide member 36 such that smooth extension 100 extends through vertical bore 60. Base 102 of femur bar 98 has its bottom edges slightly chamfered as shown at 103, like the chamfered edges described in connection with base 84 of tibia bar 80. Femur bar base 102 has a bore 104 extending lengthwise therethrough. A key lock 106 protrudes from opening 104 at a position offset 7° from the bottom center of the opening. Key lock 106 is offset to compensate for the valgus angle of the femur. As is known to those skilled in the art, the valgus angle typically has a magnitude of 5°-8°. However, the valgus angle may be less than 5° or greater than 8°. It is to be understood that key lock 106 may be offset from the bottom center of bore 104 by any amount and still remain within the contemplation of the present invention. Alternatively, a plurality of femur bars having a key lock offset at a variety of different angular displacements may be provided.

The positioning of the femur bar in guide member 36 is critical in that key lock 106 must be oriented to one side or the other depending upon whether the left knee or right knee is being resected. When resecting the right knee, the femur bar is inserted into the guide member such that key lock 106 is to the left of center (when viewing the guide member from the front). When resecting the left knee, the femur bar is inserted into the guide member such that key lock 106 is to the right of center. Thus, the apparatus of the present invention is universally applicable regardless of which knee joint is being resected.

With the femur bar properly inserted into guide member 36 and the knee still in extension with shorter portion 35 positioned in an upward direction, the femur bar and guide member inserted thereon are placed onto the guide rod such that bore 104 of femur bar 98 slides onto shorter portion 35 of the guide rod. Key lock 106 in bore 104 engages key seat 90 in shorter portion 35 of the guide rod to prevent the guide member from rotating relative to the longitudinal axis extending through the shorter portion of the guide rod.

As shown in FIG. 5A, the guide member is then slidably positioned along smooth extension 100 of femur bar 98 until the top edge, identified as 107, of base 102 is aligned with the appropriate mark 94, 96, which was determined by verifying the flexion gap. When top edge 107 is properly aligned, guide member pins 66 are pressed into the anterior distal femur to prevent the guide member from moving. Cap 62 is then threaded tightly onto threaded portion 35 of guide rod 32.

Referring now to FIG. 6, the knee is once again placed in flexion, and the guide member is already properly positioned for resecting the distal femur without the need for any manual alignment. An oscillating saw is inserted into center slots 52 of the guide member, and the distal femur is resected. Cap 62 is then loosened, guide member pins 66 are disengaged, and the femur guide rod supporting the guide member and femur bar are then removed. Any remaining portion of the distal femur may then be removed by using the previously resected portions as a leveling guide.

An important feature of the present invention resides in the fact that all of the resections are made with the knee in flexion. This reduces the danger of cutting the popliteal artery. Another important feature of the present invention is that the extension gap is in effect measured from the resected proximal tibia (see discussion in connection with FIG. 4). However, the alignment of the distal femur resection is made, without any "eyeball" techniques, by using the reference point established by the femur guide rod instead of using the resected proximal tibia as a reference point.

Still another important feature of the present invention is that overall alignment of the triplanar resections is assured even though they are aligned independently of each other. Furthermore, the simplified instrumentation of the present invention is designed such that the proximal tibial resection and the distal femoral resection are perpendicular to an imaginary axis extending through the hip joint, knee joint, and ankle joint and such that the distal femoral condylar resections are parallel to said imaginary axis. Yet, these resections are made without any direct reference to this imaginary axis.

The method of the present invention also establishes the flexion gap first. An extension gap equal to the flexion gap is then established by means of the present invention. This method eliminates the possibility that the flexion gap will be too small, thereby requiring the distal femoral condylar resections to be made too deep. It is to be understood that "flexion gap" as used herein means the perpendicular distance between the resected surface of the proximal tibia and the resected surface of the posterior distal femoral condyles when the knee is in flexion. Likewise, "extension gap" as used herein means the perpendicular distance between the resected surface of the proximal tibia and the resected surface of the distal femur when the knee is in extension.

The present invention results in a resected knee joint whereby the proximal tibial resection is parallel to the distal femoral condylar resections when the knee is in flexion and the proximal tibial resection is parallel to the distal femoral resection when the knee is in extension. As discussed above, the proximal tibial and distal femoral resections are perpendicular to said imaginary axis. These parallel and perpendicular relationships of the resections are what applicant refers to as "triplanar." These triplanar resections are important for stable functioning of a knee prosthesis.

In an alternate embodiment of the present invention, a modified femur bar 108, as shown in FIG. 7A, may be provided. The modified femur bar has a smooth extended portion 110 and a generally rectangular base 112, which are similar to those of femur bar 98. A second shorter extended portion 114 extends from the top of the base 112 and has two key seats 116 disposed 180° apart. A bore 118 in base 112 does not have a key lock. Thus, the modified femur bar with the guide member inserted thereon may rotate freely about shorter portion 35 of guide rod 32. In such case, key seat 90 of guide rod 32 may be eliminated.

Figure 7B:
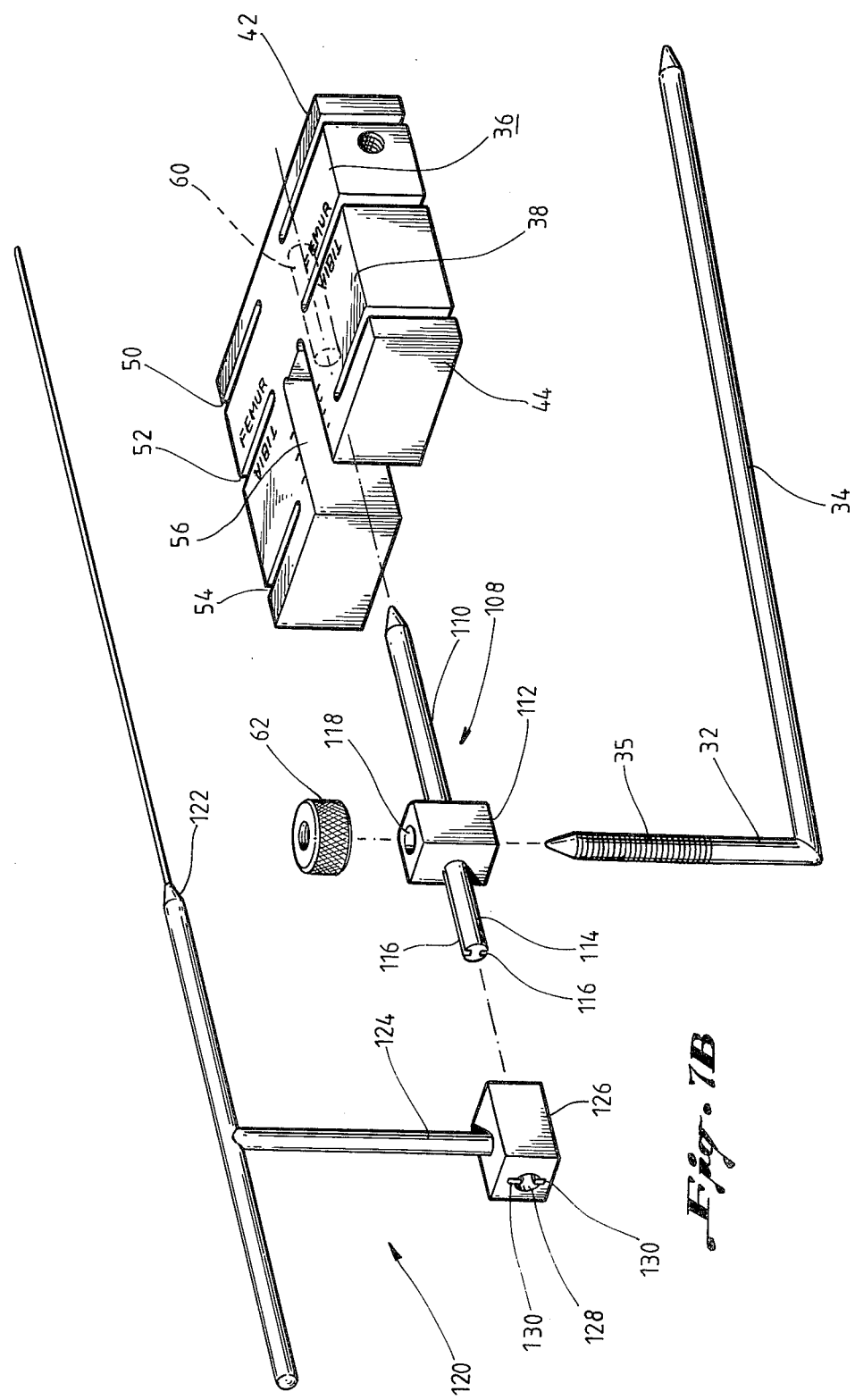
FIG. 7B is an illustrative view of a pointer for use with the modified femur bar of FIG. 7A.

In order to properly align the guide member to compensate for the valgus angle, a pointer 120 is provided as shown in FIG. 7B. The pointer includes an elongated portion 122 which is affixed to a shorter portion 124 extending perpendicular to the elongated portion 122. The shorter portion is affixed to a generally rectangular base 126. Base 126 has a bore 128 extending lengthwise therethrough and parallel to elongated portion 122. Bore 128 has a pair of key locks 130 which are disposed 180° apart. Key locks 130 are adapted to cooperate with Key seats 116 disposed on shorter extension 114 of modified femur bar 108.

When the guide member and the modified femur bar inserted therein are placed onto guide rod 32 with the knee in extension, pointer 120 may be slidably disposed onto shorter extension 114 of modified femur bar 108. Before implanting guide member pins 66, the guide member and modified femur bar may be rotated relative to shorter portion 35 of guide rod 32, such that pointer 120 is aligned with the axis extending through the hip joint, as shown schematically in FIG. 7C. Thus, the modified femur bar in cooperation with the pointer enables the guide member to be aligned at the proper valgus angle, regardless of whether the valgus angle is 5°, 8°, 12°, or any other angular measurement.

In another embodiment, a modified tibia bar 132 may be provided, as shown in FIG. 8. Modified tibia bar 132 with its threaded extension 133 is identical to tibia bar 80, except that the modified tibia bar has a shorter smooth extension portion 134 extending from the top of its base 136. Shorter extension 134 has a pair of key seats 138 disposed 180° apart for cooperating with key locks 130 of pointer 120. Also, a bore 140 in base 136 is provided without a key lock. With the modified tibia bar inserted into inverted guide member 36 and placed onto threaded portion 77 of guide rod 73 inserted into the tibia, pointer 120 may be placed onto shorter extension 134 to properly align the guide member, such that the pointer is parallel to the axis extending through the ankle joint. Thus, the modified tibia bar in cooperation with the pointer enables the proper alignment of the guide member regardless of the shape of the tibia.

As the bone resections are triplanar, as described above, overall alignment of the resected knee joint is ensured even though pointer 120 is aligned with only one of the extreme leg joints (the ankle joint when making the proximal tibial resection and the hip joint when making the distal femoral resection).

The apparatus and method of the present invention provide a simplified and improved system for making the triplanar bone resections of the knee joint. The guide member eliminates the necessity for a different type of guide component for each triplanar resection, thereby ensuring proper alignment of a knee prosthesis with the axis extending through the hip joint, the knee joint, and the ankle joint. Furthermore, the triplanar knee resection system of the present invention ensures equal flexion and extension gaps while providing for proper valgus alignment.

It is to be understood that the apparatus of the present invention will admit of other embodiments. The detailed description is given only to facilitate understanding of the invention by those skilled in the art and should not be construed as limiting the invention.

What is claimed is:

1. A method for making triplanar bone resections for total knee replacement, including the steps of:

resecting the proximal tibia such that it is perpendicular to an imaginary axis extending through the ankle joint, knee joint, and hip joint;

resecting the anterior and posterior distal femoral condyles such that they are parallel to each other and perpendicular to said axis when the knee is in flexion;

determining the flexion gap;

inserting an L-shaped femur guide rod into the medullary canal of the femur, the femur guide rod having a first portion and a second portion disposed at a right angle with respect to said first portion, the first portion being inserted in said canal;

placing the knee in extension;

partially extending said guide rod relative to said femur such that the outer surface of the second portion abuts the resected proximal tibia;

affixing a guide member having a first planar slot therein onto the second portion of said guide rod such that said slot is disposed perpendicular to the femoral medullary canal and relative to said canal to compensate for the valgus angle and such that said slot is spaced from the outer surface of the second portion a distance equal to the flexion gap;

placing the knee in flexion, while maintaining said guide rod relative to the distal femur; and resecting the distal femur in reference to said slot while the knee is in flexion.

2. The method of claim 1, wherein said step of resecting the proximal tibia comprises:

inserting an L-shaped tibia guide rod into the medullary canal of the tibia with the knee in flexion, the tibia guide rod having a first portion and a second portion disposed at a right angle therewith, the first portion being inserted in said canal;

stabilizing the tibia guide rod such that said rod is substantially coplanar with the tibial medullary canal;

affixing said guide member onto the second portion of the tibia guide rod such that said planar slot is disposed perpendicular to the tibial medullary canal; and resecting the proximal tibia in reference to said slot while the knee is in flexion.

3. The method of claims 1 or 2, wherein said guide member includes second and third planar slots therein and wherein said step of resecting the anterior and posterior distal femoral condyles comprises:

affixing said guide member onto the second portion of the femur guide rod such that said second and third slots are disposed parallel to the femoral medullary canal and perpendicular to the tibial medullary canal, said second and third slots being parallel to said first slot; and resecting the anterior and posterior distal femoral condyles in reference to said second and third slots, respectively.

4. The method of claim 3, wherein said step of resecting the anterior and posterior distal femoral condyles is accomplished prior to said step of resecting the proximal tibia.

5. The method of claim 3, wherein said step of resecting the proximal tibia is accomplished prior to said step of resecting the anterior and posterior distal femoral condyles.

6. The method of claim 1, wherein said step of resecting the distal femur in reference to said slot is accomplished by resecting said distal femur through said slot while the knee is in flexion.

7. The method of claim 1, wherein said L-shaped femur guide rod includes markings on its second portion for determining the flexion gap, and wherein said guide member includes markings corresponding to said markings on said guide rod, and wherein said method further comprises the steps of:

orienting said L-shaped femur guide rod such that said second portion of said guide rod is generally perpendicular to the resected surface of the proximal tibia;

determining the flexion gap in response to said marks on said second portion of said guide rod; and positioning said guide member relative to said guide rod in response to said marks on said guide member and said determined flexion gap.

8. The method of claim 1, wherein said guide member includes an indicator which lies perpendicular to said first planar slot and wherein said step of affixing a guide member having a first planar slot therein on a second portion of said guide rod such that said slot is disposed perpendicular to the femoral medullary canal and relative to said canal to compensate for the valgus angle comprises the step of aligning with the axis extending from the guide member through the hip joint.

* * * * *